United States Patent [19]

Nelson et al.

[11] Patent Number: 4,686,234

[45] Date of Patent: Aug. 11, 1987

[54] MYCOPHENOLIC ACID DERIVATIVES IN THE TREATMENT OF INFLAMMATORY DISEASES, IN PARTICULAR RHEUMATOID ARTHRITIS

[75] Inventors: Peter H. Nelson, Los Altos; Anthony C. Allison; Elsie M. Eugui, both of Belmont, all of Calif.

[73] Assignee: Syntex (U.S.A) Inc., Palo Alto, Calif.

[21] Appl. No.: 803,041

[22] Filed: Nov. 27, 1985

[51] Int. Cl.$^4$ .................................... C07D 307/88
[52] U.S. Cl. ................................. 514/469; 549/310
[58] Field of Search ...................... 549/310; 514/469

[56] References Cited

U.S. PATENT DOCUMENTS

| | | | |
|---|---|---|---|
| 3,705,894 | 12/1972 | Gerzon et al. | 548/253 |
| 3,825,571 | 7/1974 | Mori et al. | 549/310 |
| 3,853,919 | 12/1974 | Mori et al. | 548/964 |
| 3,880,995 | 4/1975 | Jones | 514/27 |
| 3,903,071 | 9/1975 | Holmes | 536/18.1 |

FOREIGN PATENT DOCUMENTS

| | | |
|---|---|---|
| 2237549 | 2/1973 | Fed. Rep. of Germany . |
| 48-86861 | 11/1973 | Japan . |
| 48-86860 | 11/1973 | Japan . |
| 57-24380 | 2/1982 | Japan . |
| 57-024380 | 2/1982 | Japan . |
| 57-183776 | 11/1982 | Japan . |
| 183777 | 12/1982 | Japan . |
| 1157100 | 8/1967 | United Kingdom . |

OTHER PUBLICATIONS

J. Antibiotics, vol. 29, pp. 286-291 (1976).
Cancer Research, vol. 36, pp. 2923-2927 (1976).

*Primary Examiner*—Jane T. Fan

*Attorney, Agent, or Firm*—Ellen J. Wise; Tom M. Moran; Alan M. Krubiner

[57] ABSTRACT

Compounds useful for treating inflammatory diseases, in particular rheumatoid arthritis, represented by the formula:

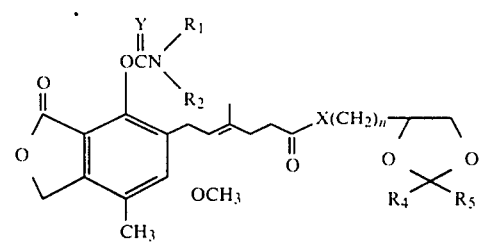

and the pharmaceutically acceptable salts thereof, wherein:

$R_1$ is H or lower alkyl having 1 to 6 carbon atoms;
$R_2$ is H, lower alkyl having 1 to 6 carbon atoms or

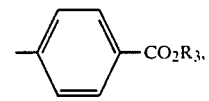

in which $R_3$ is H, lower alkyl having 1 to 6 carbon atoms or a pharmaceutically acceptable cation;
$R_4$ and $R_5$ are each independently H or lower alkyl having 1 to 6 carbon atoms;
X and Y are each independently O or S; and
n is an integer of 1-6.

19 Claims, No Drawings

MYCOPHENOLIC ACID DERIVATIVES IN THE TREATMENT OF INFLAMMATORY DISEASES, IN PARTICULAR RHEUMATOID ARTHRITIS

BACKGROUND OF THE INVENTION

1. Field of the Invention

This invention concerns mycophenolic acid derivatives as agents in the treatment of inflammatory diseases, in particular rheumatoid arthritis.

2. Previous Disclosures

Inflammatory diseases, in particular rheumatoid arthritis, have been treated with a variety of compounds representing many structural classes, including, for example, the corticosteroids, aspirin and related compounds, derivatives of arylacetic and arylpropionic acids, relatives of phenylbutazone, gold salts and penicillamine and its derivatives. However, no representative of any of these classes of compounds is regarded as ideal.

Mycophenolic acid is a weakly-active antibiotic found in the fermentation broth of Penicillium brevicompactum. It has now been discovered that certain mycophenolic acid derivatives and related compounds are useful as agents in the treatment of inflammatory diseases, in particular rheumatoid arthritis.

Compounds somewhat structurally similar to the compounds of the present invention are described in U.S. Pat. Nos. 3,705,894; 3,853,919; 3,868,454; 3,880,995, in Japanese Pat. No. J 57024380, in the J. Antibiot., 29(3), 275–85, 286–91 (1976), and in Cancer Research, 36(8), 2923–7 (1976). The disclosed compounds are described as having anti-tumor, immunosuppressive, anti-viral, anti-arthritic and anti-psoriastic activities.

SUMMARY OF THE INVENTION

One aspect of the invention concerns novel compounds of the formula:

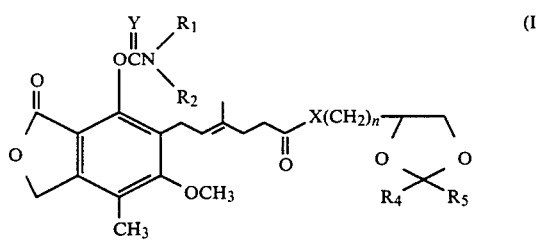

(I)

and the pharmaceutically acceptable salts thereof, wherein:

$R_1$ is H or lower alkyl having 1 to 6 carbon atoms;
$R_2$ is H, lower alkyl having 1 to 6 carbon atoms or

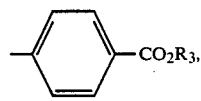

in which $R_3$ is H, lower alkyl having 1 to 6 carbon atoms or a pharmaceutically acceptable cation;
$R_4$ and $R_5$ are each independently H or lower alkyl having 1 to 6 carbon atoms;
X and Y are each independently O or S; and
n is an integer of 1–6.

In two other aspects, the invention relates to a pharmaceutical composition containing a therapeutically effective amount of a compound of Formula I admixed with at least one pharmaceutically acceptable excipient and to a method of treating inflammatory diseases, including in particular, rheumatoid arthritis, in a mammal by administering to a mammal in need of such treatment a compound of Formula I.

Finally, the invention relates to a novel process for preparing the compounds of Formula I and includes the preparation of several novel intermediates.

DETAILED DESCRIPTION OF THE INVENTION

Definitions

As used herein:

"Lower alkyl" means a branched or unbranched saturated hydrocarbon chain containing 1 to 6 carbon atoms, such as methyl, ethyl, propyl, isopropyl, tert-butyl, butyl, n-hexyl and the like.

"Alkoxy" means the group —OR wherein R is lower alkyl as herein defined.

Some compounds of Formula I may be converted to a base addition salt by virtue of the presence of a carboxylic acid group. The term "Pharmaceutically acceptable cation" refers to the cation of such salts. The cation is chosen to retain the biological effectiveness and properties of the corresponding free acids and not to be biologically or otherwise undesirable. The cations derived from inorganic bases include sodium, potassium, lithium, ammonium, calcium, magnesium and the like. Cations derived from organic bases include those formed from primary, secondary and tertiary amines, such as isopropylamine, diethylamine, trimethylamine, pyridine, cyclohexylamine, ethylene diamine, monoethanolamine, diethanolamine, triethanolamine and the like.

The compounds of this invention are derivatives of "mycophenolic acid" which has the structure shown as Formula (II) and has a ring system numbered as shown:

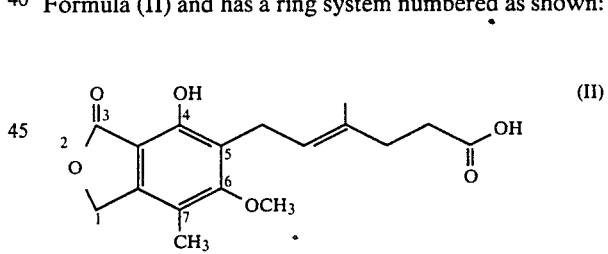

(II)

The compounds of the invention will be named using the above shown numbering system as 6-(1,3-dihydro-4-hydroxy-6-methoxy-7-methyl-3-oxo-5-isobenzofuranyl)-4-methyl-4-hexenoic acid derivatives. Following are examples of how representative compounds of Formula I are named:

A compound of Formula I wherein $R_1$ is methyl, $R_2$ is ethyl, $R_4$ and $R_5$ are methyl, X and Y are O and n is 1 is named "(±)-(2,2-dimethyl-1,3-dioxolan-4-yl)methyl(E)-6[1,3-dihydro-4-(N-ethyl-N-methylcarbamoyloxy)-6-methoxy-7-methyl-3-oxo-5-isobenzofuranyl]-4-methyl-4-hexenoate."

A compound of Formula I wherein $R_1$ is H, $R_2$ is 4-methoxycarbonylphenyl, $R_4$ is ethyl, $R_5$ is hexyl, X and Y are S and n is 4 is named "(±)-[1-(2-ethyl-2-hexyl-1,3-dioxolan-4-yl)but-4-yl](E)-6(1,3-dihydro-4-[N-(4-methoxycarbonylphenyl)-thiocarbamoyloxy]-6- methoxy-7-methyl-3-oxo-5-isobenzofuranyl)-4-methyl-4-thiohexenoate."

Methods of Preparation

The compounds of the invention (compounds of Formula I) are prepared by the procedures described below, and illustrated by the following reaction scheme:

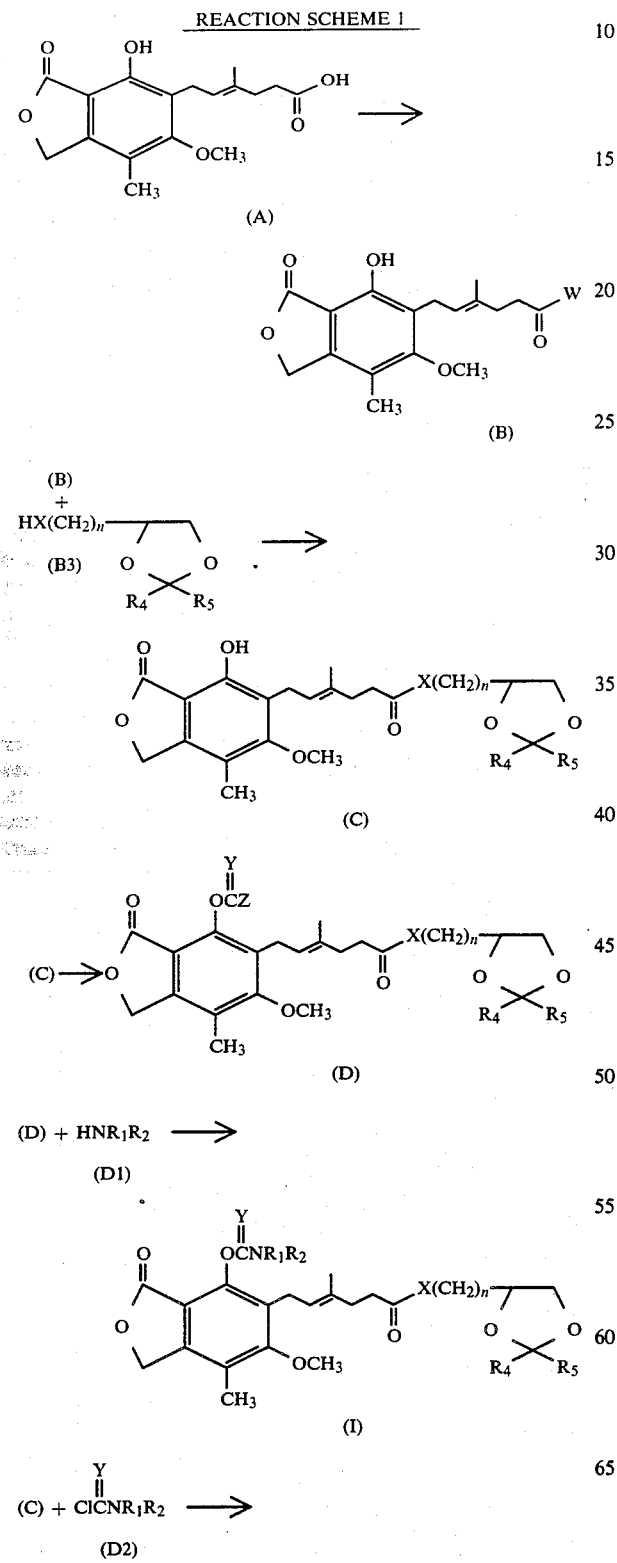

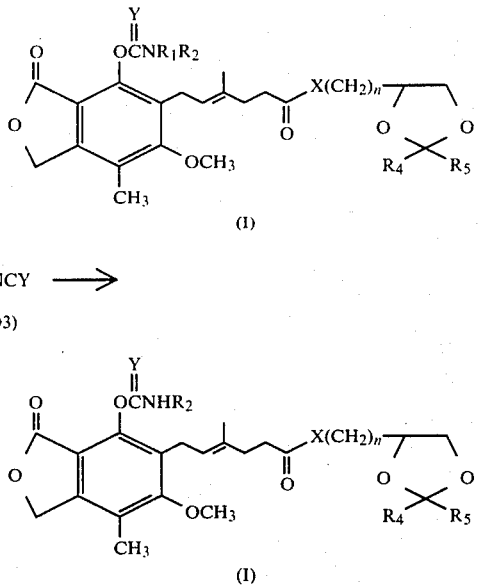

To prepare the compounds of the invention, the mycophenolic acid of Formula A is first converted to an activated carbonyl derivative of Formula B in which W is a leaving group, such as halo, N-carbonylimidazole, alkoxy, acyloxy or the like, chosen to be capable of displacement by a compound of Formula B3 in the presence of a base. The compounds of Formula B are prepared by standard means well known in the chemical arts. For example, the compound of Formula B where W is chloro is made by reaction with from 1.0 to 10 molar equivalents, preferably 4.0 molar equivalents, of an inorganic acid halide such as phosphorus trichloride, phosphorus pentachloride or preferably thionyl chloride, optionally in the presence of a catalytic amount of an N,N-disubstituted amide, such as N,N-dimethylformamide in an inert organic solvent such as benzene, toluene, tetrahydrofuran, diethyl ether, chloroform or preferably dichloromethane. The reaction is conducted at a temperature of about 0° to 90° C., preferably about 25° C., for about 1–12 hours, preferably about three hours.

The product of Formula B is then reacted with about 1–10 molar equivalents, preferably about 4.0 molar equivalents, of a compound of Formula B'in an inert organic solvent as defined above, preferably dichloromethane. The reaction takes place in the presence of from 1–10 molar equivalents, preferably about 5 molar equivalents, of an inorganic base such as sodium carbonate, potassium bicarbonate or the like, or a tertiary organic base, such as triethylamine, N-methylpiperidine or preferably pyridine. The reaction is conducted at 0°–25° C., preferably about 5° C., for thirty minutes to six hours, preferably about one hour. The resulting product of Formula C is isolated and purified by conventional means.

The compound of Formula C is then converted to an activated carbonyl or thiocarbonyl derivative of Formula D, in which Z is a leaving group chosen to be capable of displacement by an amine of Formula D1. For example, Z may be halo, N-carbonylimidazole, trichloromethoxy, optionally substituted phenoxy, such as 2,4-dichlorophenoxy, 4-methoxyphenyl, and the like. For example, the compound of Formula D where Z is chloro is made by reaction of C with from 1-10 molar equivalents, preferably about 2 molar equivalents, of phosgene or thiophosgene in an inert organic solvent as defined above, preferably benzene. The reaction takes place in the presence of from 1-5 molar equivalents, preferably about 2 molar equivalents of a tertiary organic base such as triethylamine or preferably pyridine. The reaction is conducted at from 0°-50° C., preferably about 25° C., for about 1-72 hours, preferably about 18 hours, and then filtered. Evaporation of the filtrate under vacuum affords the compound of Formula D where Z is Cl.

Alternatively, the compound of Formula C is reacted as above, substituting an appropriately substituted alkyl or aryl chloroformate or chlorothioformate for phosgene or thiophosgene, giving the compound of Formula D where Z is the correspondingly substituted alkoxy or aryloxy.

Alternatively, the compound of Formula C is reacted as above, substituting N,N'-carbonyldiimidazole or N,N'-thiocarbonyldiimidazole for phosgene or thiophosgene, giving the compound of Formula D where Z is N-carbonylimidazole or N-thiocarbonylimidazole.

The products of the reactions described herein can be isolated and purified by any suitable separation or purification procedure, such as, for example, filtration, extraction, crystallization, column chromatography, thin-layer chromatography, thick-layer chromatography, preparative low or high pressure liquid chromatography, or a combination of these procedures. Specific illustrations are described in the Examples. However, other equivalent separation or purification procedures can be used.

The salt products are also isolated by conventional means. For example, the reaction mixtures can be evaporated to dryness and the salts then further purified by standard methods such as those listed above.

The compound of Formula D are then converted to the desired compounds of Formula I by treating with the appropriate reagent, as described below.

COMPOUNDS OF FORMULA I

Compounds of Formula I can be prepared by treating the appropriately substituted compound of Formula D with an appropriate amine of Formula D1, thereby converting the —OCYZ group to the corresponding carbamate or thiocarbamate. To carry out this process, the compound of Formula D is dissolved in an inert organic solvent as defined above, preferably tetrahydrofuran, and reacted with from about 2-5 molar equivalents, preferably about 2-3 molar equivalents, of the appropriate amine of Formula D1 in solution in an inert solvent as defined above, preferably tetrahydrofuran. The reaction takes place at a temperature of about 0°-40° C., preferably about 25° C., for about 1-10 hours, preferably about 4 hours, at a pressure of about 1-5 atmospheres, preferably at atmospheric pressure. When the reaction is substantially complete, the product compound of Formula 1 is isolated by conventional means and if desired converted to a pharmaceutically acceptable salt.

Alternatively, the reaction is carried out in the presence of from 1-5 molar equivalents, preferably 2 molar equivalents, of a tertiary organic base or an inorganic base, as defined above. The compound of Formula D is reacted with from 1-4 molar equivalents, preferably about 1.2 molar equivalents, of the appropriate amine of Formula D1 in an inert organic solvent, as defined above.

Alternatively, compounds of Formula I are made directly from compounds of Formula C, by reaction with an appropriately substituted carbamoyl or thiocarbamoyl chloride of Formula D2. To carry out this process, the compound of Formula C is dissolved in an inert organic solvent as defined above, preferably tetrahydrofuran, and reacted with from 1-4 molar equivalents, preferably about 1.2 molar equivalents, of the appropriate carbamoyl or thiocarbamoyl chloride of Formula D2 in the presence of a tertiary organic base or inorganic base as defined above. The reaction takes place at a temperature of about 0°-40° C., preferably about 25° C., for about 1-10 hours, preferably about 4 hours. When the reaction is substantially complete, the product of Formula I is isolated by conventional means.

Compounds of Formula I where $R_1$ is H can also be made by reacting a compound of Formula C with an appropriately substituted isocyanate or isothiocyanate of Formula D3. To carry out this process, the compound of Formula C is dissolved in an inert organic solvent as defined above, preferably toluene, and reacted with from 1-5 molar equivalents, preferably about 2 molar equivalents, of an isocyanate or isothiocyanate of Formula D3. The reaction takes place at a temperature of about 10°-100° C., preferably about 50° C., for about 1-10 hours, preferably about 4 hours. When the reaction is substantially complete, the product of Formula I is isolated by conventional means.

The compounds of Formula I have one or more asymmetric centers. Accordingly, they may be prepared in either optically active form or as a racemic mixture. Unless otherwise specified, the compounds described herein are all racemic mixtures. However, the scope of the invention described and claimed encompasses the individual optical isomers as well as the racemic forms of the compounds of Formula I.

The diastereomers and/or enantiomers of compounds of Formula I can be separated by conventional resolution procedures, well known to those skilled in the art. For example, by fractional crystallization, by chromatography, by selective biological degradation or by carrying out the preparation shown in Reaction Scheme 1 using optically active isomers of Formula B3. The separation of the optically active isomers of Formula B3 is described below. Compounds of Formula I which contain a carboxyl group can be separated into their enantiomers by fractional crystallization of the salts formed with an optically active base such as brucine, cinchonidine and the like.

SALTS OF COMPOUNDS OF FORMULA I

Some of the compounds of Formula I may be converted to a base addition salt by virtue of the presence of a carboxylic acid group, i.e., $R_3$ is a pharmaceutically acceptable cation.

The conversion is accomplished by treatment with a stoichiometric amount of an appropriate base, such as potassium carbonate, sodium bicarbonate, ammonia, ethylene diamine, monoethanolamine, diethanolamine, triethanolamine and the like. Typically, the free acid is dissolved in a polar organic solvent such as ethanol or methanol, and the base added in water, ethanol or methanol. The temperature is maintained at 0°-50° C. The resulting salt precipitates spontaneously or may be brought out of solution with a less polar solvent.

The base addition salts of the compounds of Formula I may be decomposed to the corresponding free acids by treating with an excess of a suitable acid, such as hydrochloric acid or sulfuric acid, typically in the presence of aqueous solvent, and at a temperature of between 0° and 50° C. The free acid form is isolated by conventional means, such as extraction with an organic solvent.

PREPARATION OF STARTING MATERIALS

The compounds of Formula I are prepared from mycophenolic acid, the compound of Formula A, which is commercially available.

Some of the compounds of Formula B3 are commercially available. Alternatively, the compounds of Formula B3 may be prepared by reacting together the compounds of Formula B1 and B2 in the presence of an acid catalyst, as shown in Reaction Scheme 2.

REACTION SCHEME 2

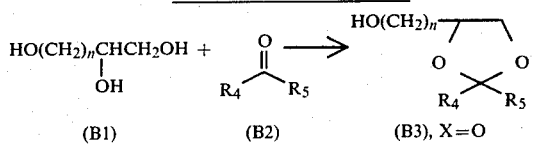

where $R_4$, $R_5$ and n are as defined above.

The reaction is discussed in greater detail in *Organic Functional Group Preparation*, 2nd Edition, Vol III, by Sandler and Karo, pp 4–17, which is incorporated herein by reference.

The triols of Formula B1 can be prepared from the appropriate olefinic alcohol, e.g., allyl alcohol, 7-octen-1-ol, etc., by reaction with aqueous sodium hypochlorite in the presence of osmium tetroxide, as described in the supplement to the 2nd edition of *Rodds Chemistry of Carbon Compounds*, Vol. $1^E$, p 145, which is incorporated herein by reference.

Compounds of Formula B3 where X is S are obtained from the corresponding compounds where X is O as shown in Reaction Scheme 3.

REACTION SCHEME 3

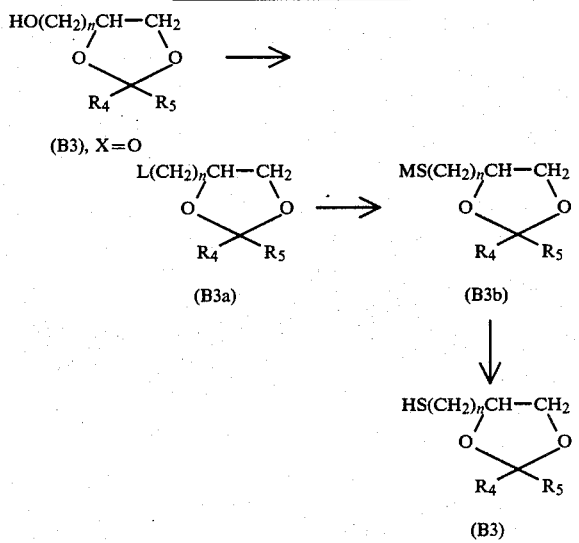

The compounds of Formula B3 where X is O are first converted to a compound B3a where L is a leaving group, by reaction with, for example, p-toluenesulfonyl chloride. The group L is then displaced with a sulfur nucleophile such as potassium thioacetate or thiourea to afford a compound of Formula B3b in which M is $CH_3CO$— or $NH_2C(NH)$—. Hydrolysis of B3b then produces the compound of Formula B3 where X is S.

Compounds of Formula B3 may have one or more asymmetric centers. The individual isomers, if not commercially available or described in the chemical literature, can be made from the racemic compounds by conventional resolution procedures. For example, the racemic compound of Formula B3 can be converted into an ester or thioester with an optically active acid, such as, for example, α-methylphenylacetic acid or camphoric acid. The individual diastereomeric isomers are then separated by conventional means, for example, crystallization or chromatography, and then subjected to basic hydrolysis to afford the separate enantiomers of compound B3.

The compounds of Formula D1 are commercially available. Alternatively, they can be prepared by standard methods known to those skilled in the chemical art. The compounds of Formula D1 wherein $R_2$ is phenyl having a substituent $COOR_3$ where $R_3$ is lower alkyl are prepared from the compounds of Formula D1 where $R_3$ is H—for example, by reaction of the appropriate compound of Formula D1 with an excess of the alcohol $R_3OH$ in the presence of an acid catalyst. The reaction is described in greater detail in *Organic Functional Group Preparations*, 2nd Edition, Vol. I, by Sandler and Karo, pp. 289–309, which is incorporated herein by reference.

The compounds of Formula D2 are either available commercially or can be prepared by, for example, reaction of a secondary amine of Formula D1 with phosgene (Y=O) or thiophosgene (Y=S). Compounds of Formula D2 wherein $R_1$ is H can be prepared by the reaction of an isocyanate or isothiocyanate of Formula D3 with an excess of dry hydrochloric acid in an inert solvent. These reactions are described in greater detail in *Comprehensive Organic Chemistry*, Vol. 2, by Barton and Ollis, pp. 1088–1090, which is incorporated herein by reference.

Any alkyl or aryl chloroformates or chlorothioformates that are not commercially available are prepared, for example, by reaction of phosgene or thiophosgene with one equivalent of the appropriate alcohol or phenol in the presence of a base. The reactions are described in greater detail in *Comprehensive Organic Chemistry*, by Barton and Ollis, Vol 2, pp 1078–1083 and Vol 3, pp 432–4, which is incorporated herein by reference.

The compounds of Formula D3 that are not commercially available are prepared by reaction of an appropriately substituted primary amine ($R_2NH_2$) with phosgene or thiophosgene. The reaction is discussed in further detail in *Organic Functional Group Preparations*, 2nd Edition, Vol. 1, by Sandler and Karo, pp. 364–365, which is incorporated herein by reference.

In summary, the compounds of the present invention are made by the procedures outlined below:

(1) The process for preparing compounds of Formula I wherein:

$R_1$ is H or lower alkyl having 1 to 6 carbon atoms;
$R_2$ is H, lower alkyl having 1 to 6 carbon atoms or

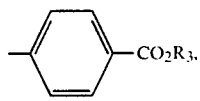

in which $R_3$ is H, lower alkyl having 1 to 6 carbon atoms or a pharmaceutically acceptable cation;
$R_4$ and $R_5$ are each independently H or lower alkyl having 1 to 6 carbon atoms;
X and Y are each independently O or S;
n is an integer of 1–6. comprises:

(a) reacting a compound of the formula

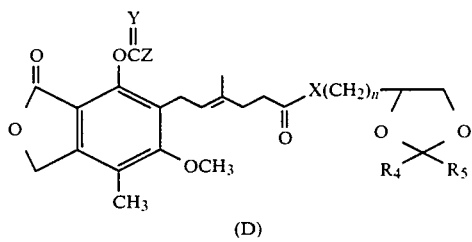

wherein $R_4$, $R_5$, X, Y and n are as defined above, and —CYZ is an activated carbonyl derivative, where Z is as defined above, with an appropriate amine of the formula $R_1R_2NH$, wherein $R_1$ and $R_2$ are as defined above; or (b) converting the free acid of the compound of Formula I, where appropriate, with a base to a pharmaceutically acceptable salt; or (c) converting a base addition salt of the compound of Formula I with an acid to the corresponding free acid.

(d) converting a base addition salt of the compound of Formula I to another pharmaceutically acceptable base addition salt.

(2) Alternatively, a process for preparing a compound of Formula I, above, comprises:

(a) reacting a compound of the formula:

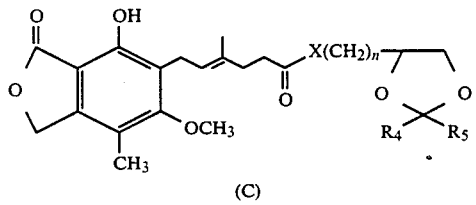

wherein $R_4$, $R_5$, X, and n are as defined above, with a carbamoyl chloride of the formula

or an isocyanate of the formula $R_2NCY$ wherein $R_1$, $R_2$ and Y are as defined above; or (b) converting the free acid, where appropriate, of the compound of Formula I with a base to a pharmaceutically acceptable salt; or (c) converting a base addition salt of the compound of Formula I with an acid to the corresponding free acid.

(d) converting a base addition salt of the compound of Formula I to another pharmaceutically acceptable base addition salt.

UTILITY AND ADMINISTRATION

The compounds of Formula I have been shown in standard laboratory tests to be useful in treating chronic inflammatory diseases, including models of rheumatoid arthritis, in mammals. Accordingly, the compounds of Formula I, their salts, and pharmaceutical compositions containing them, may be used in treating inflammatory diseases with an immunologically based component, particularly rheumatoid arthritis, in mammals by administering a therapeutically effective amount of a compound of Formula I to a mammal in need thereof. Antiinflammatory activity can be determined by the method described by C. M. Pearson in *Proc. Soc. Exp. Biol. Med.*, 91:95–101, (1956) utilizing adjuvant-induced arthritis in rats. This method is described in detail in Example 10 hereinbelow. Rheumatoid arthritis is also characterized as an autoimmune disease. Activity against autoimmune diseases can be determined by the method described by Grieg, et al. in *J. Pharmacol. Exp. Ther.* 173:85 (1970) using experimental allergic encephalomyelitis induced in rats. The method is described in Example 11 below.

Administration of the active compounds and salts described herein can be effected via any medically acceptable mode of administration for agents which control inflammation, rheumatoid arthritis and associated pain. These methods include but are not limited to oral, parenteral and otherwise systemic routes of administration. Oral administration is preferred, depending of course, on the disorder being treated. The compounds are administered in a therapeutically effective amount either alone or in combination with a suitable pharmaceutically acceptable excipient.

Depending on the intended mode of administration, the compounds of this invention may be incorporated in any pharmaceutically acceptable dosage form, such as, for example, tablets, suppositories, pills, capsules, powders, liquids, suspensions, emulsions, aerosols, or the like. Preferable means of administration are unit dosage forms suitable for single administration of precise dosages, or sustained release dosage forms for continuous administration. Preferably the dosage form will include a pharmaceutically acceptable excipient and an active compound of Formula I, or a pharmaceutically acceptable salt thereof, and, in addition, may include other medicinal agents, pharmaceutical agents, carriers, excipients, adjuvants, stabilizers, etc. Depending on parameters such as mode of administration, type of composition, and activity of the compound, the pharmaceutical composition may contain 1–95 percent by weight active ingredient with the remainder being excipient.

For solid dosage forms, non-toxic solid carriers include but are not limited to, for example, pharmaceutical grades of mannitol, lactose, starch, magnesium stearate, sodium saccharin, the polyalkylene glycols, talcum, cellulose, glucose, sucrose, and magnesium carbonate. An example of a solid dosage form of the compounds of this invention is a suppository containing propylene glycol as the carrier. Liquid pharmaceutically administerable dosage forms can, for example, comprise a solution or suspension of an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see *Remington's Pharmaceutical Sciences,* Mack Publishing Company, Easton, P.A., 16th Edition, 1980. The composition or formulation to be administered will, in any event, contain a quantity of the active compound(s) in an amount effective to alleviate the symptoms of the subject being treated.

For oral administration, a pharmaceutically acceptable non-toxic dosage form may contain any of the normally employed excipients, such as, for example pharmaceutical grades of mannitol, lactose, starch, magnesium stearate, sodium saccharin, talcum, cellulose, glucose, sucrose, magnesium carbonate, and the like. Such compositions take the form of solutions, suspensions, tablets, pills, capsules, powders, sustained release formulations and the like. Such dosage forms may contain 1%–95% active ingredient, preferably 25–70%.

The amount of active compound administered will, of course, depend on the subject being treated, the severity of the affliction, the manner of administration and the judgment of the prescribing physician. However, a therapeutically effective dosage of compounds of the instant invention is in the range of 1–100 mg/kg/day, preferably about 5–30 mg/kg/day, and most preferably about 10 mg/kg/day. For an average 70 kg human, this would amount to 70 mg–7 g per day, or preferably about 700 mg/day.

PREFERRED EMBODIMENTS

One preferred subgroup of the family of compounds of the present invention includes those compounds of Fomula I wherein each of X and Y is oxygen. Preferred embodiments of this subgroup are compounds of Formula I wherein $R_4$ and $R_5$ are identical. Another preferred subgroup is wherein each of X and Y is oxygen, $R_4$ and $R_5$ are independently methyl or ethyl, and n is 1 or 2. Of these, more preferred are the compounds of Formula I wherein $R_1$ is H and $R_2$ is

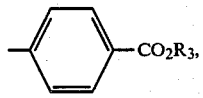

especially those compounds wherein $R_4$ and $R_5$ are each methyl and n is 1. Particularly preferred among these compounds is the compound wherein $R_2$ is 4-carboxyphenyl, namely ($\pm$)-(2,2-dimethyl-1,3-dioxolan-4-yl)methyl(E)-6{1,3-dihydro-4-[N-(4-carboxyphenyl)-carbamoyloxy]-6-methoxy-7-methyl-3-oxo-5-isobenzofuranyl}-4-methyl-4-hexenoate, as the racemic compound or its dextro and levo isomers.

Yet another preferred subgroup includes those compounds of Formula I wherein X is sulfur and Y is oxygen. Of these, one class of preferred embodiments are compounds of Formula I wherein $R_4$ and $R_5$ are identical; a second class are those wherein $R_4$ and $R_5$ are independently methyl or ethyl, and n is 1 or 2. Of the latter, more preferred are the compounds of Formula I wherein $R_1$ is H and $R_2$ is

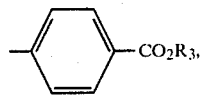

especially those compounds wherein $R_4$ and $R_5$ are each methyl and n is 1. Particularly preferred among these compounds is the compound wherein $R_2$ is 4-carboxyphenyl, namely($\pm$)-(2,2-dimethyl-1,3-dioxolan-4-yl)methyl (E)-6{1,3-dihydro-4-[N-(4-carboxyphenyl)-carbamoyloxy]-6-methoxy-7-methyl-3-oxo-5-isobenzofuranyl}-4-methyl-4-thiohexenoate, as the racemic compound or its dextro and levo isomers.

The following preparations and examples serve to illustrate the invention. They should not be construed as in any way narrowing or limiting the scope of the invention as claimed.

PREPARATION I

Preparation of 2,2-Dimethyl-1,3-dioxolan-4-ylmethanethiol and Related Compounds of Formula B3

(a) To a solution of 7.2 g of 2,2-dimethyl-1,3-dioxolan-4-ylmethanol in 40 ml of pyridine at 0° C. was added 11.3 g of p-toluenesulfonyl chloride in portions. The solution was kept at 25° C. for 48 hours, then poured into water and extracted with diethyl ether. The organic solution was washed twice with water, once with dilute hydrochloric acid and once with dilute sodium carbonate solution. The organic solution was dried with magnesium sulfate and evaporated under vacuum to yield ($\pm$)-2,2-dimethyl-1,3-dioxolan-4-ylmethyl p-toluenesulfonate.

(b) A mixture of 13.3 g of the above product and 7.2 g of potassium thioacetate in 300 ml of acetone was refluxed for 10 hours. The resulting mixture was filtered, most of the solvent evaporated off under vacuum and the remaining solution poured into diethyl ether. The solution was washed with water, the organic solvent removed under vacuum and the residue distilled under vacuum, giving ($\pm$)2,2-dimethyl-1,3-dioxolan-4-ylmethyl thioacetate, having a boiling point between 83° C. and 87° C. at a pressure of 0.1 mm Hg.

(c) To a solution of 100 mgs of sodium in 100 ml of methanol was added 5.0 g of the ($\pm$)2,2-dimethyl-1,3-dioxolan-4-ylmethyl thioacetate. The mixture was left at 25° C. for 6 days, and the solvent then removed under vacuum. The residue was dissolved in diethyl ether, washed with water and the organic solution dried over magnesium sulfate. Evaporation of the solvent and distillation of the residue under vacuum gave ($\pm$)-2,2-dimethyl-1,3-dioxolan-4-ylmethanethiol, with a boiling point of 78°–82° C. at 15 mm Hg pressure.

(d) In a similar manner, starting from the appropriately substituted compounds of Formula B3, where X is O, the following representative compounds of Formula B3 where X is S are prepared as described in paragraphs (a) to (c) of this preparation:

1,3-dioxolan-4-ylmethanethiol;
2-methyl-1,3-dioxolan-4-ylmethanethiol;
2-methyl-2-ethyl-1,3-dioxolan-4-ylmethanethiol;
2,2-diethyl-1,3-dioxolan-4-ylmethanethiol;
2-methyl-2-n-butyl-1,3-dioxolan-4-ylmethanethiol;
2-isopropyl-2-n-butyl-1,3-dioxolan-4-ylmethanethiol;
2,2-dihexyl-1,3-dioxolan-4-ylmethanethiol;
1(2,2-dimethyl-1,3-dioxolan-4-yl)ethane-2-thiol;

1(2,2-diethyl-1,3-dioxolan-4-yl)ethane-2-thiol;
1(2-ethyl-2-isopropyl-1,3-dioxolan-4-yl)ethane-2-thiol;
1(2-methyl-2-n-propyl-1,3-dioxolan-4-yl)ethane-2-thiol;
1(2-isopropyl-2-isopentyl-1,3-dioxolan-4-yl)ethane-2-thiol;
1(2,2-dimethyl-1,3-dioxolan-4-yl)propane-3-thiol;
1(2-methyl-2-isopropyl-1,3-dioxolan-4-yl)propane-3-thiol;
1(2-n-butyl-2-isobutyl-1,3-dioxolan-4-yl)propane-3-thiol;
1(2,2-dimethyl-1,3-dioxolan-4-yl)butane-4-thiol;
1(2-sec-butyl-2-isopropyl-1,3-dioxolan-4-yl)butane-4-thiol;
1(2,2-dimethyl-1,3-dioxolan-4-yl)pentane-5-thiol;
1(2-isobutyl-2-butyl-1,3-dioxolan-4-yl)pentane-5-thiol;
1(2,2-dimethyl-1,3-dioxolan-4-yl)hexane-6-thiol; and
1(2,2-dihexyl-1,3-dioxolan-4-yl)hexane-6-thiol.

EXAMPLE 1

(A) Preparation of (±)-(2,2-dimethyl-1,3-dioxolan-4-yl)methyl(E)-6{1,3-dihydro-4-[N-(4-carboxyphenyl)carbamoyloxy]-6-methoxy-7-methyl-3-oxo-5-isobenzofuranyl}-4-methyl-4-hexenoate and related compounds of Formula 1

A solution of 500 mgs of mycophenolic acid in 10 ml of dichloromethane containing 0.5 ml of thionyl chloride and 0.05 ml of N.N-dimethylformamide was maintained at 25° C. for 3 hours. The volatile components were then distilled off under vacuum to obtain crude (E)-[1,3-dihydro-4-hydroxy-6-methoxy-7-methyl-3-oxo-5-isobenzofuranyl]-4-methyl-4-hexenoyl chloride.

A solution of this compound in 4 ml of dry dichloromethane was cooled in ice and a mixture of 0.51 ml of pyridine and 825 mg of (±)-2,2-dimethyl-1,3-dioxolan-4-ylmethanol was added. After 1 hour the solution was evaporated to dryness and the residue chromatographed on silica gel, eluting with ether, to afford as an oil (±)-2,2-dimethyl-1,3-dioxolan-4-yl)methyl(E)-(1,3-dihydro-4-hydroxy-6-methoxy-7-methyl-3-oxo-5-isobenzofuranyl)-4-methyl-4-hexenoate.

A solution of this oil was dissolved in 10 ml of dry benzene and 0.23 ml of pyridine, and 3 ml of a solution of 12.5% phosgene in benzene added. The mixture was stirred overnight at 25° C., filtered and the filtrate evaporated under vacuum to afford crude (±)-2,2-dimethyl-1,3-dioxolan-4-yl)methyl(E)-(1,3-dihydro-4-chlorocarbonyloxy-6-methoxy-7-methyl-3-oxo-5-isobenzofuranyl)-4-methyl-4-hexenoate.

This chloroformate was dissolved in 5 ml of dry tetrahydrofuran and a solution of 391 mgs of p-aminobenzoic acid in 3 ml of tetrahydrofuran added. After 4 hours, the reaction mixture was diluted with ethyl acetate and washed with dilute hydrochloric acid. The organic solution was dried over magnesium sulfate, filtered and the filtrate evaporated under vacuum. The residue was triturated with ether to afford the title compound, (±)-(2,2-dimethyl-1,3-dioxolan-4-yl)methyl(E)-6{1,3-dihydro-4-[N-(4-carboxyphenyl)carbamoyloxy]-6-methoxy-7-methyl-3-oxo-5-isobenzofuranyl}-4-methyl-4-hexenoate, having a melting point of 175° C. to 177° C.

(B) In a similar manner, but staring instead with (±)-2,2-dimethyl-1,3-dioxolan-4-yl methanethiol, whose preparation is described in preparation 1, the following compound of Formula I was obtained:

(±)-(2,2-dimethyl-1,3-dioxolan-4-yl)methyl (E)-6{1,3-dihydro-4[N-(4-carboxyphenyl)carbamoyloxy]-6-methoxy-7-methyl-3-oxo-5-isobenzofuranyl}4-methyl-4-thiohexenoate, having a melting point of 195° C. to 197° C.

(C) Similarly, starting with mycophenolic acid and substituting other appropriate compounds of Formula B3 and D1 for (±)-2,2-dimethyl-1,3-dioxolan-4-ylmethanol and p-aminobenzoic acid respectively, the following representative compounds of Formula I, where X is O, as racemic mixtures or their optically active isomers are prepared:

| $R_1$ | $R_2$ | $R_4$ | $R_5$ | n | Y |
|---|---|---|---|---|---|
| H | 4-carboxyphenyl | H | H | 1 | O |
| H | 4-carboxyphenyl | H | methyl | 1 | O |
| H | 4-carboxyphenyl | methyl | ethyl | 1 | O |
| H | 4-carboxyphenyl | methyl | methyl | 2 | O |
| H | 4-carboxyphenyl | ethyl | ethyl | 1 | S |
| H | 4-carboxyphenyl | methyl | n-butyl | 1 | O |
| H | 4-carboxyphenyl | ethyl | ethyl | 2 | O |
| H | 4-carbomethoxyphenyl | methyl | ethyl | 1 | O |
| H | 4-carboxyphenyl | i-propyl | n-butyl | 1 | S |
| H | 4-carboxyphenyl | methyl | methyl | 3 | O |
| methyl | 4-carboxyphenyl | methyl | methyl | 4 | O |
| H | 4-carboxyphenyl | methyl | methyl | 6 | S |
| ethyl | ethyl | methyl | methyl | 1 | O |
| i-propyl | 4-carboxyphenyl | ethyl | i-propyl | 2 | O |
| n-butyl | 4-carboxyphenyl | methyl | i-propyl | 3 | O |
| H | H | methyl | methyl | 1 | O |
| ethyl | ethyl | methyl | n-propyl | 2 | S |
| ethyl | n-butyl | i-butyl | n-butyl | 3 | O |
| n-butyl | n-hexyl | i-propyl | sec-butyl | 4 | O |
| n-hexyl | 4-carboxyphenyl | methyl | methyl | 1 | O |
| n-hexyl | n-hexyl | n-hexyl | n-hexyl | 1 | O |
| H | 4-carboxyphenyl | n-hexyl | n-hexyl | 1 | O |
| H | H | i-propyl | i-pentyl | 2 | S |
| H | 4-carboxyphenyl | methyl | methyl | 6 | O |
| H | 4-n-hexyloxycarbonylphenyl | methyl | methyl | 6 | O |

(D) Similarly, the following representative compounds of Formula I, where X is S, as racemic mixtures or their optically active isomers are prepared:

| $R_1$ | $R_2$ | $R_4$ | $R_5$ | n | Y |
|---|---|---|---|---|---|
| H | 4-carboxyphenyl | H | H | 1 | O |
| H | 4-carboxyphenyl | H | methyl | 1 | O |
| H | 4-carboxyphenyl | methyl | ethyl | 1 | O |
| H | 4-carboxyphenyl | methyl | methyl | 2 | O |
| H | 4-carboxyphenyl | ethyl | ethyl | 1 | S |
| H | 4-carboxyphenyl | methyl | n-butyl | 1 | O |
| H | 4-carboxyphenyl | ethyl | ethyl | 2 | O |
| H | 4-carbomethoxyphenyl | methyl | ethyl | 1 | O |
| H | 4-carboxyphenyl | i-propyl | n-butyl | 1 | S |
| H | 4-carboxyphenyl | methyl | methyl | 3 | O |
| methyl | 4-carboxyphenyl | methyl | methyl | 4 | O |
| H | 4-carboxyphenyl | methyl | methyl | 6 | S |
| ethyl | ethyl | methyl | methyl | 1 | O |
| i-propyl | 4-carboxyphenyl | ethyl | i-propyl | 2 | O |
| n-butyl | 4-carboxyphenyl | methyl | i-propyl | 3 | O |
| H | H | methyl | methyl | 1 | O |
| ethyl | ethyl | methyl | n-propyl | 2 | S |
| ethyl | n-butyl | i-butyl | n-butyl | 3 | O |
| n-butyl | n-hexyl | i-propyl | sec-butyl | 4 | O |
| n-hexyl | 4-carboxyphenyl | methyl | methyl | 1 | O |
| n-hexyl | n-hexyl | n-hexyl | n-hexyl | 1 | O |
| H | 4-carboxyphenyl | n-hexyl | n-hexyl | 1 | O |
| H | H | i-propyl | i-pentyl | 2 | S |
| H | 4-carboxyphenyl | methyl | methyl | 6 | O |
| H | 4-n-hexyloxycarbonylphenyl | methyl | methyl | 6 | O |

EXAMPLE 2

Conversion of Free Acid to Salt

One molar equivalent of sodium hydroxide in water is added to a methanolic solution of 1.0 g of (±)-(2,2-dimethyl-1,3-dioxolan-4-yl)methyl(E)-6{1,3-dihydro-4-[N-(4-carboxyphenyl)carbamoyloxy]-6-methoxy-7-methyl-3-oxo-5-isobenzofuranyl}-4-methyl-4-hexenoate. The solvent is removed under vacuum and the residue recrystallized to give the sodium salt of (±)-(2,2-dimethyl-1,3-dioxolan-4-yl)methyl(E)-6{1,3-dihydro-4-[N-(4-carboxyphenyl)-carbamoyloxy]-6-methoxy-7-methyl-3-oxo-5-isobenzofuranyl}-4-methyl-4-hexenoate.

EXAMPLE 3

Conversion of Salt to Free Acid 1.0 g of the sodium salt of (±)-(2,2-dimethyl-1,3-dioxolan-4-yl)-methyl(E)-6{1,3-dihydro-4-[N-(4-carboxyphenyl)-carbamoyloxy]-6-methoxy-7-methyl-3-oxo-5-isobenzofuranyl}-4-methyl-4-hexenoate suspended in ether is stirred with 2 molar equivalents of dilute aqueous sulfuric acid until the salt is completely dissolved. The organic layer is separated, washed with water, dried over magnesium sulfate and evaporated to yield (±)-(2,2-dimethyl-1,3-dioxolan-4-yl)methyl(E)-6{1,3-dihydro-4[N-(4-carboxyphenyl)carbamoyloxy]-6-methoxy-7-methyl-3-oxo-5-isobenzofuranyl}-4-methyl-4-hexenoate.

EXAMPLE 4

Direct Interchange of Basic Salts 1.0 g of the ammonium salt of (±)-(2,2-dimethyl-1,3-dioxolan-4-yl)methyl(E)-6{1,3-dihydro-4-[N-(4-carboxyphenyl)carbamoyloxy]-6-methoxy-7-methyl-3-oxo-5-isobenzofuranyl}-4-methyl-4-hexenoate is dissolved in methanol containing one molar equivalent of sodium hydroxide and the solution evaporated to dryness under vacuum. The residue is recrystallized to give the sodium salt of (±)-(2,2-dimethyl-1,3-dioxolan-4-yl)methyl(E)-6{1,3-dihydro-4-[N-(4-carboxyphenyl)carbamoyloxy]-6-methoxy-7-methyl-3-oxo-5-isobenzofuranyl}-4-methyl-4-hexenoate.

EXAMPLES 5–9

In Examples 5 through 9, the active ingredient is (±)-(2,2-dimethyl-1,3-dioxolan-4-yl)methyl(E)-6{1,3-dihydro-4-[N-(4-carboxyphenyl)carbamoyloxy]-6-methoxy-7-methyl-3-oxo-5-isobenzofuranyl}-4-methyl-4-hexenoate. However other compounds of Formula I and the pharmaceutically acceptable salts thereof may be substituted therein:

EXAMPLE 5

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 6

| Ingredients | Quantity per tablet, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 7

| Ingredients | Quantity per tablet, mgs. |
| --- | --- |
| Active ingredient | 108 |
| lactose | 15 |
| cornstarch | 25 |
| magnesium stearate | 2 |

The above ingredients are mixed and introduced into a hard-shell gelatin capsule.

EXAMPLE 8

| Ingredients | Quantity per tablet, mgs. |
| --- | --- |
| Active ingredient | 150 |
| lactose | 92 |

The above ingredients are mixed and introduced into a hard-shell gelatin capsule.

EXAMPLE 9

A solution preparation buffered to a pH of 7 is prepared having the following composition:

| Ingredients | |
| --- | --- |
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| distilled water | q.s. to 100 ml |

EXAMPLE 10

Determination Of Anti-Inflammatory Activity Utilizing Adjuvant-Induced Arthritis In The Rat Protocol:

This procedure is a modification of a system initially described by Pearson, C. M., *Proc. Soc. Exp. Biol. Med.*, 91:95–101 (1956).

Female Simonsen albino rats weighing 160–180 g received 0.1 ml of a suspension in paraffin oil of heat-killed M. *Mycobacterium butyricum* (10 mg/ml) by means of an intradermal injection into the proximal ¼ of the tail on day 0. Beginning on day 1, the test material was administered orally in an aqueous vehicle (0.5 ml/dose) twice each day for 17 days. On day 18 the intensity of the swelling of the four foot pads and tail was determined utilizing a scoring system in which the swelling in the four paws was scored 0–4 for each paw and the tail swelling was scored 0–3, such that the total maximum score was 19. The compounds of the present invention show anti-inflammatory activity when tested by this method.

EXAMPLE 11

Determination Of Autoimmune Activity Utilizing Experimental Allergic Encephalomyelitis Protocol:

This procedure is a modification of a procedure initially described by Grieg, et al., *J. Pharmacol. Exp. Ther.* 173:85 (1970).

On day 1, Experimental Allergic Encephalomyelitis was induced by giving an 0.1 ml sub-plantar injection into the dorsum of the right hind paw of an emulsion consisting of 15 mg (wet weight) of syngeneic spinal cord tissue, 0.06 ml of Freund's Incomplete Adjuvant (Difco), 0.04 ml of sterile 0.9% saline, and 0.2 mg of heat killed and dried *Mycobacterium butyricum* (Difco). On days 12-17, clinical evaluations were obtained for each animal. The animals were considered positive if flaccid hind limb paralysis was present on one or more days.

What is claimed is:

1. A compound of the formula:

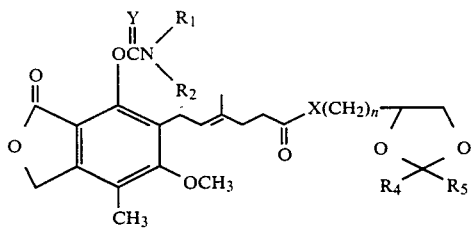

or a pharmaceutically acceptable salt thereof, wherein:

$R_1$ is H or lower alkyl having 1 to 6 carbon atoms;
$R_2$ is H, lower alkyl having 1 to 6 carbon atoms or

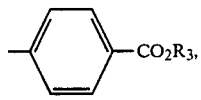

in which $R_3$ is H, lower alkyl having 1 to 6 carbon atoms or a pharmaceutically acceptable cation;
$R_4$ and $R_5$ are each independently H or lower alkyl having 1 to 6 carbon atoms;
X and Y are each independently O or S;
n is an integer of 1-6.

2. The compound of claim 1 wherein each of X and Y is O, or a pharmaceutically acceptable salt thereof.

3. The compound of claim 2 wherein $R_4$ and $R_5$ are identical, or a pharmaceutically acceptable salt thereof.

4. The compound of claim 2 wherein $R_4$ and $R_5$ are independently methyl or ethyl and n is 1 or 2, or a pharmaceutically acceptable salt thereof.

5. The compound of claim 4 wherein $R_1$ is H and $R_2$ is

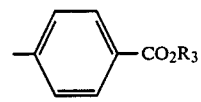

or a pharmaceutically acceptable salt thereof.

6. The compound of claim 5 wherein $R_4$ and $R_5$ are each methyl and n is 1, or a pharmaceutically acceptable salt thereof.

7. The compound of claim 6 wherein: $R_2$ is

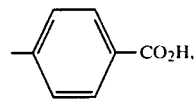

namely ($\pm$)-(2,2-dimethyl-1,3-dioxolan-4-yl)methyl(E)-6{1,3-dihydro-4-[N-(4-carboxyphenylcarbamoyloxy]-6-methoxy-7-methyl-3-oxo-5-isobenzofuranyl}-4-methyl-4-hexenoate, or a pharmaceutically acceptable salt thereof.

8. The compound of claim 7 wherein the compound is the dextro isomer, or a pharmaceutically acceptable salt thereof.

9. The compound of claim 7 wherein the compound is the levo isomer, or a pharmaceutically acceptable salt thereof.

10. The compound of claim 1 wherein X is S and Y is O, or a pharmaceutically acceptable salt thereof.

11. The compound of claim 10 wherein $R_4$ and $R_5$ are identical, or a pharmaceutically acceptable salt thereof.

12. The compound of claim 10 wherein $R_4$ and $R_5$ are independently methyl or ethyl and n is 1 or 2, or a pharmaceutically acceptable salt thereof.

13. The compound of claim 12 wherein $R_1$ is H and $R_2$ is

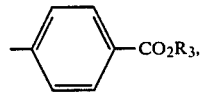

or a pharmaceutically acceptable salt thereof.

14. The compound of claim 13 wherein $R_4$ and $R_5$ are each methyl and n is 1, or a pharmaceutically acceptable salt thereof.

15. The compound of claim 14 wherein: $R_2$ is

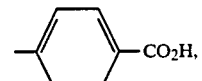

namely ($\pm$)-(2,2-dimethyl-1,3-dioxolan-4-yl)methyl(E)-6{1,3-dihydro-4-[N-(4-carboxyphenylcarbamoyloxy]-6-methoxy-7-methyl-3-oxo-5-isobenzofuranyl}-4-methyl-4-thiohexenoate, or a pharmaceutically acceptable salt thereof.

16. The compound of claim 15 wherein the compound is the dextro isomer, or a pharmaceutically acceptable salt thereof.

17. The compound of claim 15 wherein the compound is the levo isomer, or a pharmaceutically acceptable salt thereof.

18. A pharmaceutical composition for use in treating inflammatory diseases which comprises a therapeutically effective amount of a compound of claim 1 or a pharmaceutically acceptable salt thereof, in admixture with one or more pharmaceutically acceptable excipients.

19. A method of treating inflammatory diseases including rheumatoid arthritis which method comprises administering to a mammal in need of such treatment a therapeutically effective amount of a compound of claim 1, or a pharmaceutically acceptable salt thereof.

* * * * *